(12) United States Patent
Bleser et al.

(10) Patent No.: US 7,769,601 B1
(45) Date of Patent: Aug. 3, 2010

(54) APPARATUS AND METHOD FOR ACCESSING PHARMACY INFORMATION AND ORDERING PRESCRIPTIONS

(75) Inventors: Michael Bleser, Deerfield, IL (US); Tim McCauley, Libertyville, IL (US); George Riedl, Libertyville, IL (US); Randy Roesner, Lake Villa, IL (US); Ron Weinert, Mundelein, IL (US)

(73) Assignee: Walgreen Co., Deerfield, IL (US)

( * ) Notice: Subject to any disclaimer, the term of this patent is extended or adjusted under 35 U.S.C. 154(b) by 702 days.

(21) Appl. No.: 09/715,872

(22) Filed: Nov. 15, 2000

Related U.S. Application Data

(60) Provisional application No. 60/165,479, filed on Nov. 15, 1999.

(51) Int. Cl.
*G06F 19/00* (2006.01)
*G06Q 30/00* (2006.01)
(52) U.S. Cl. ............................................. 705/3; 705/26
(58) Field of Classification Search .................. 705/2, 705/20, 3
See application file for complete search history.

(56) References Cited

U.S. PATENT DOCUMENTS

| 5,597,995 | A | | 1/1997 | Williams et al. | |
|---|---|---|---|---|---|
| 5,619,991 | A | | 4/1997 | Sloane | |
| 5,737,539 | A | * | 4/1998 | Edelson et al. ................. | 705/3 |
| 5,758,095 | A | * | 5/1998 | Albaum et al. ................. | 705/2 |
| 5,790,785 | A | | 8/1998 | Klug et al. | |
| 5,797,515 | A | | 8/1998 | Liff et al. | |
| 5,801,755 | A | | 9/1998 | Echerer | |

(Continued)

FOREIGN PATENT DOCUMENTS

EP 0 921 488 A1 6/1999

(Continued)

OTHER PUBLICATIONS

Anonymous, "CVS, Merck-Medco in E-commerce Alliance," Oct. 25, 1999, Chain Drug Review, vol. 21, No. 18, 2 pages.*

(Continued)

*Primary Examiner*—Robert W Morgan
*Assistant Examiner*—Rachel L Porter
(74) *Attorney, Agent, or Firm*—Francis C. Kowalik, Walgreen Co.; Randall G. Rueth

(57) ABSTRACT

A method and system for implementing an on-line pharmacy website that allows customers of a particular pharmacy company to order new prescriptions, refill prescriptions and transfer existing prescription. The method and system also afford a user access to personal information such as their prescription history. Integration of an internet server hosting the website with a pharmacy company's intranet server and customer database allows a customer full on-line access to their information stored by the pharmacy company, as well as access to drug information. A further feature includes allowing the user to format and print their prescription history and records. Another feature of the system and method includes a "click-free" registration of customers with the website by entry of customer data by company personnel at any company location connected to the intranet server, such as at a pharmacy store. Personnel solicit information from the customer including, for example, an e-mail address. Registration of the customer is then performed by the company personnel and website access information is, in turn, communicated to the customer via e-mail.

20 Claims, 15 Drawing Sheets

U.S. PATENT DOCUMENTS

| | | | | |
|---|---|---|---|---|
| 5,845,255 | A | * | 12/1998 | Mayaud .................... 705/3 |
| 5,907,493 | A | | 5/1999 | Boyer et al. |
| 5,911,687 | A | * | 6/1999 | Sato et al. ................ 600/300 |
| 5,915,240 | A | * | 6/1999 | Karpf ....................... 705/2 |
| 5,924,074 | A | * | 7/1999 | Evans ....................... 705/3 |
| 5,954,640 | A | * | 9/1999 | Szabo ...................... 600/300 |
| 5,970,462 | A | * | 10/1999 | Reichert ................... 705/2 |
| 5,987,519 | A | | 11/1999 | Peifer et al. |
| 6,067,524 | A | * | 5/2000 | Byerly et al. ............... 705/3 |
| 6,202,923 | B1 | * | 3/2001 | Boyer et al. .............. 235/375 |
| 6,208,973 | B1 | * | 3/2001 | Boyer et al. ................ 705/2 |
| 6,294,999 | B1 | * | 9/2001 | Yarin et al. ............. 340/573.1 |
| 6,311,163 | B1 | * | 10/2001 | Sheehan et al. ............. 705/2 |
| 6,330,491 | B1 | * | 12/2001 | Lion ....................... 700/237 |
| 6,347,329 | B1 | * | 2/2002 | Evans ...................... 709/202 |
| 6,381,577 | B1 | * | 4/2002 | Brown ...................... 705/2 |
| 6,397,190 | B1 | * | 5/2002 | Goetz ...................... 705/3 |
| 6,421,650 | B1 | * | 7/2002 | Goetz et al. ................ 705/3 |
| 6,438,451 | B1 | * | 8/2002 | Lion ....................... 700/237 |
| 6,463,417 | B1 | * | 10/2002 | Schoenberg ................ 705/2 |
| 6,464,142 | B1 | * | 10/2002 | Denenberg et al. ..... 235/462.46 |
| 6,493,427 | B1 | * | 12/2002 | Kobylevsky et al. ....... 379/67.1 |
| 6,523,009 | B1 | * | 2/2003 | Wilkins .................... 705/3 |
| 6,564,121 | B1 | * | 5/2003 | Wallace et al. ............. 700/231 |
| 6,711,460 | B1 | | 3/2004 | Reese |
| 6,735,497 | B2 | * | 5/2004 | Wallace et al. ............. 700/231 |
| 6,874,684 | B1 | * | 4/2005 | Denenberg et al. .......... 235/381 |
| 2001/0009005 | A1 | * | 7/2001 | Godin et al. ................ 705/37 |
| 2002/0035484 | A1 | * | 3/2002 | Mccormick ................ 705/2 |
| 2002/0062175 | A1 | * | 5/2002 | Lion ....................... 700/237 |
| 2002/0062230 | A1 | * | 5/2002 | Morag et al. ............... 705/3 |
| 2002/0120573 | A1 | * | 8/2002 | McCormick ................ 705/50 |
| 2002/0153411 | A1 | | 10/2002 | Wan et al. |
| 2002/0188467 | A1 | | 12/2002 | Eke |
| 2003/0074234 | A1 | | 4/2003 | Stasny |
| 2003/0149599 | A1 | | 8/2003 | Goodall et al. |
| 2003/0179287 | A1 | | 9/2003 | Kozic et al. |
| 2004/0220829 | A1 | * | 11/2004 | Baharav et al. .............. 705/2 |
| 2004/0221034 | A1 | * | 11/2004 | Kausik et al. .............. 709/224 |
| 2004/0260577 | A1 | * | 12/2004 | Dahlin et al. ............... 705/2 |
| 2006/0041330 | A1 | | 2/2006 | Ansari et al. |

FOREIGN PATENT DOCUMENTS

| | | |
|---|---|---|
| WO | WO 96 13790 | 5/1996 |
| WO | WO 0108393 A1 | 2/2001 |

OTHER PUBLICATIONS

Walgreens On-line Prefills (Website Printout Packet- printed Jul. 5, 2006) archived as Jun. 14, 1998, 13 pages.*

Anonymous, "Name Change Reflects CVS' Commitment to E-Commerce," Sep. 13, 1999, Chain Drug Review, vol. 21, No. 15, 2 pages.*

Colchamiro, "Independents look to go online," *American Druggist*, Sep. 1999, p. 1-3.

NcNaughton, "Can Net drugstores outpace the chains?" CNET News.com, Feb. 24, 1999, p. 1.

Wolverton, "Online pharmacies partner for power," CNET News.com, Oct. 8, 1999, p. 1-2.

"The Virtual Pharmacist," *Rural Electric*, vol. 60, No. 6, Mar. 2002, p. 20.

U.S. Appl. No. 09/715,872, filed Nov. 15, 2000, entitled "Apparatus and Method for Accessing Pharmacy Information and Ordering Prescriptions."

U.S. Appl. No. 11/253,252, filed Oct. 18, 2005, entitled "System for Separating and Distributing Pharmacy Order Processing."

U.S. Appl. No. 11/252,759, filed Oct. 18, 2005, entitled "System for Separating and Distributing Pharmacy Order Processing for Medication Payments."

U.S. Appl. No. 11/252,776, filed Oct. 18, 2005, entitled "System for Separating and Distributing Pharmacy Order Processing for Specialty Medication."

U.S. Appl. No. 11/253,185, filed Oct. 18, 2005, entitled "System for Separating and Distributing Pharmacy Order Processing for Prescription Verification."

U.S. Appl. No. 11/253,253, filed Oct. 18, 2005, entitled "System for Separating and Distributing Pharmacy Order Processing for Out of Stock Medication."

U.S. Appl. No. 11/252,947, filed Oct. 18, 2005, entitled "System for Separating and Distributing Pharmacy Order Processing for Compound Medication."

U.S. Appl. No. 11/252,775, filed Oct. 18, 2005, entitled "Method and Apparatus for Inter-Pharmacy Workload Balancing."

U.S. Appl. No. 11/253,096, filed Oct. 18, 2005, entitled "Method and Apparatus for Inter-Pharmacy Workload Balancing Using Resource Function Assignments."

* cited by examiner

APPARATUS AND METHOD FOR ACCESSING PHARMACY INFORMATION AND ORDERING PRESCRIPTIONS

RELATED APPLICATIONS

This application claims the benefit of U.S. provisional application No. 60/165,479, filed Nov. 15, 1999.

BACKGROUND OF THE INVENTION

The present invention relates to a method and apparatus for accessing pharmacy information and ordering prescriptions via a network connection, and more particularly to access via a network, such as the Internet, to personal pharmacy information and personal prescription ordering.

In the area of Internet commerce, the use of websites to relay product information and also allow customers to order goods or services via the internet is well-known. Within this arena the dispensing of pharmaceutical information and the filling of medical prescriptions is known. Typically such websites are proprietary and allow customers of a particular pharmacy to order prescriptions from that particular pharmacy or pharmacy company. Since many of these companies consist of a chain of member stores, the use of internet for dispensing drug information and for ordering prescriptions becomes more desirable.

Prior art on-line pharmacies include linking a number of users accessing the internet to a network server owned by the pharmacy in order to view pharmaceutical information and order prescriptions to be delivered either via mail or to be picked up at a particular store location of the pharmacy company by the user. Past attempts, however, have consisted of an internet server for communicating with the pharmacy customers via the internet and accepting prescription orders. These orders are then, in turn, faxed or e-mailed to the particular pharmacy store, for example, where a pharmacist or technician then verifies the prescription and fills the prescription order. Such attempts, however, have limitations in that the server connected to the internet is not interfaced with a company data base of customers prescription and health histories, thus creating more manual steps to be undertaken such as e-mailing or faxing prescriptions and access by the pharmacist or technician to another repository of health and prescription records for the particular user.

There is therefore a need for an apparatus and method of on-line pharmacies that integrates customer health and prescription records with a network server that is effecting communication with users via the internet. Additionally, the prior art systems also make access of health and prescription records kept by the pharmacy company difficult to access by the end users since no integration exists between the internet network server and the information repositories kept by the particular pharmacy company. Hence, there is a need for a method and apparatus that affords more ease of access to prescription and health history records kept by the particular pharmacy company.

DETAILED DESCRIPTION OF THE PREFERRED EMBODIMENTS

The present teachings of the invention solve the above-described problems by integrating an internet on-line pharmacy website with an in-house internet server and customer database. This integration affords a user of the on-line website the ability to order prescriptions, wherein the prescription order is sent directly to a pharmacy store via network connections thereby eliminating the need for separate communications such as e-mail, facsimile, or telephony communication. Additionally, since the customer database and internet server are integrated with the network server the user may readily view the user's complete prescription history, as well as the ability to format and print the prescription history. Furthermore, the integration of the network server with the internet server, which serves to network the locations of all pharmacy stores owned by the particular pharmacy company to enable website registration of a particular customer/user of the pharmacy company without accessing the on-line pharmacy website, thereby effecting a "click-free" registration of customer/users. That is, for example, a user may provide e-mail information to a particular store location of the pharmacy company, which in turn registers the user via the intranet connecting the pharmacy company locations.

Figure 1:
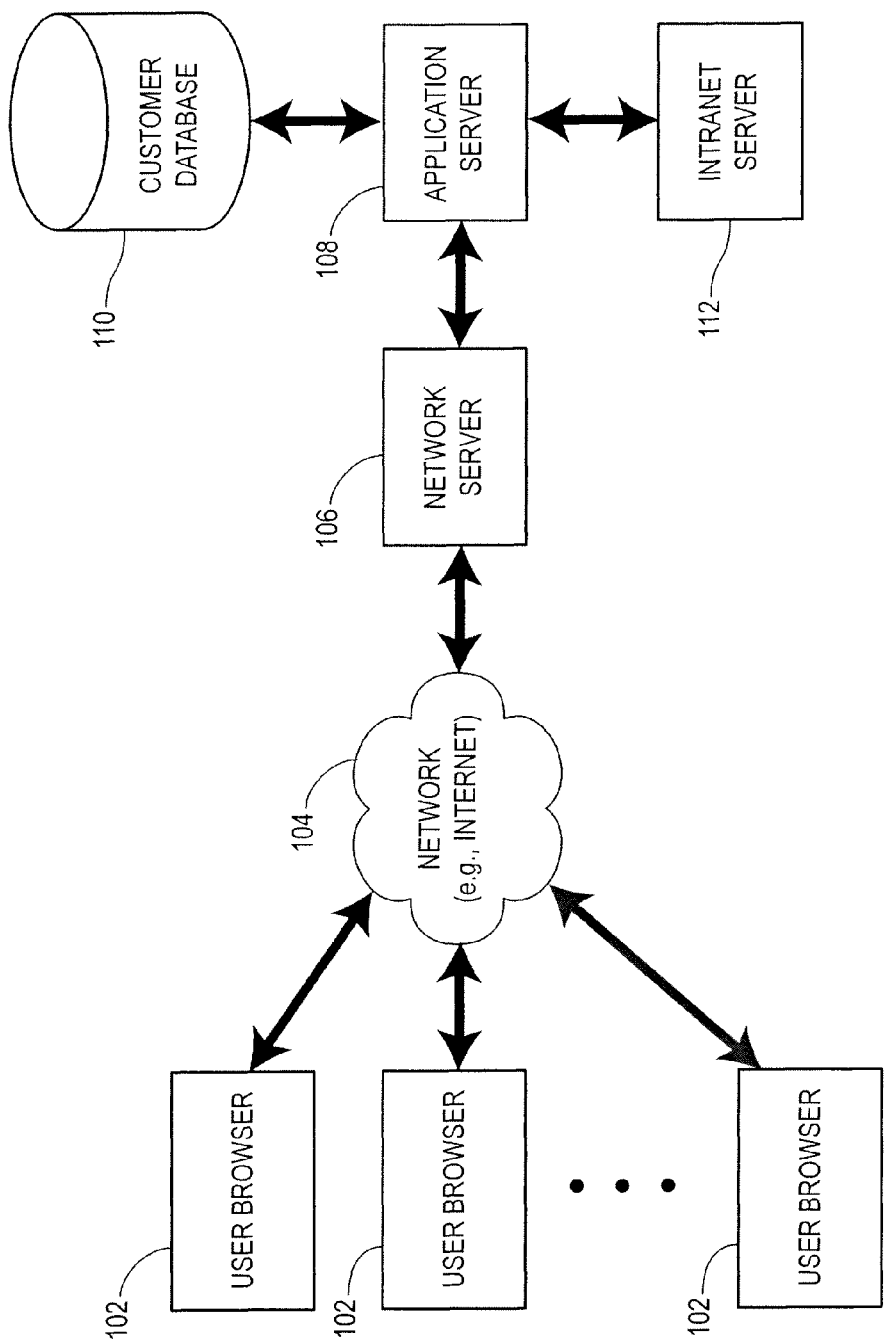
FIG. 1 illustrates a system for an on-line pharmacy according to the teachings of the present invention.

FIG. 1 illustrates an on-line pharmacy system according to the teachings of the present invention. The system includes a network server 106 that is connected to a network 104 such as the internet. One or more users via a user browser 102 may access the network server 106 via the network 104. Network server 106 is, in turn, connected to an application server 108 that enables integration of a customer data base 110 having information such as a customer's prescription history and health history. The intranet server 112 is a network internal to a pharmacy company and links pharmacy store locations with one another.

The application server 108 serves to integrate the customer data base 110, the Internet server 112, and the network server 106 so that information and services offered by the pharmacy company are available to all user browsers 102 accessing the network server 106 by the network 104.

Figure 2:
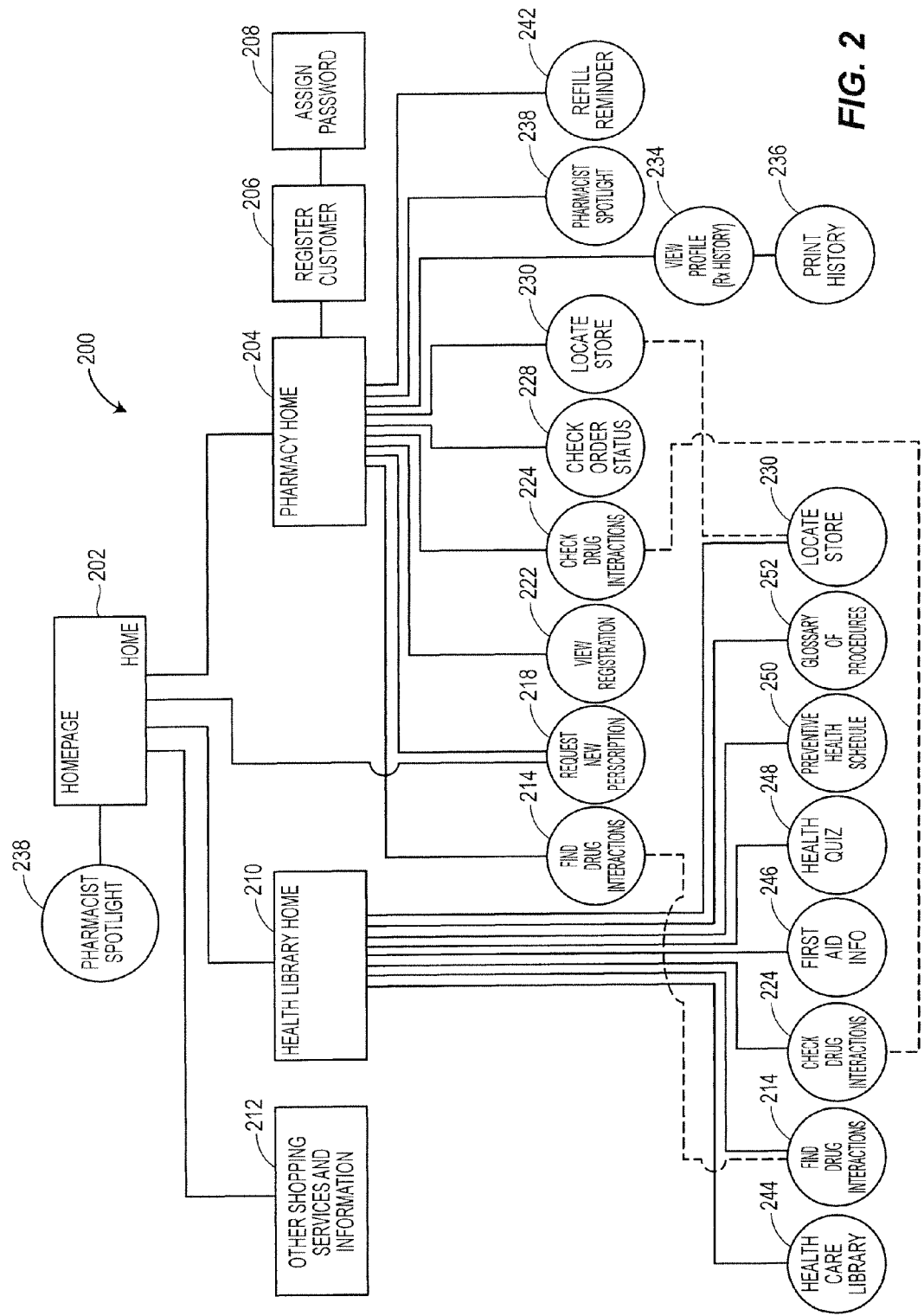
FIG. 2 illustrates a diagrammatic illustration of the organization for an internet on-line pharmacy site according to the teachings of the present invention.

FIG. 2 illustrates an exemplary website organization that can be implemented in the network server 106. An initial screen or "homepage" is shown at 202. This page within the website allows users various options that they may select including a pharmacy homepage 204 and a health library homepage 210. Additional services such as shopping services and other information (e.g., company information) 212 may be also linked with the homepage 202. Within the health library homepage 210 are various links to health information that can be provided. As shown, links to information such as a healthcare library 244, a drug interactions search page 214, a drug interactions check 224, first aid information 246, a quiz concerning health issues 248, preventative health scheduling 250, a glossary of medical procedures 252, or a store locator 230 for the particular company are shown but are not limited to just these particular types of information.

From the pharmacy homepage 204, are links to pharmacy services, information, and a customer's personal health and prescription history. Examples shown include the drug interactions search 214 which is the same as the drug interactions search linked from the health library home 210, request for a new prescription order 218, which is also preferably shown with a direct link from the homepage 202, a registration view 222 that shows a user their particular registration information within the website, the drug interaction check 224 which is also linked from the health library home 210, a status check for particular orders placed by the user 228, a pharmacy store locator 230, which is also shown linked to the health library homepage 210, a profile viewer 234 that displays a user's prescription history and other personal health information, a print history 236 that enables a user to format and print the viewed user profile from the profile viewer 234, a pharmacist spotlight that displays information concerning particular pharmacists employed by the pharmacy corporation, and a refill reminder 242 that allows a user to request a reminder such as a date that a prescription must be refilled.

Additionally from the pharmacy home page 204 is a link to a customer registration 206, which, in turn, allows a user to select a username and password as shown by block 208. This registration, however, could be linked from any portion of the website not just the pharmacy home page 204 as will be described later.

The description that follows illustrates the particular processes that are followed to perform various functions offered by the on-line pharmacy website. Each of these processes are exemplary according to a preferred embodiment of the teachings of the present invention, but could also be employed in other ways as will be appreciated by those of ordinary skill in the art.

Figure 3:
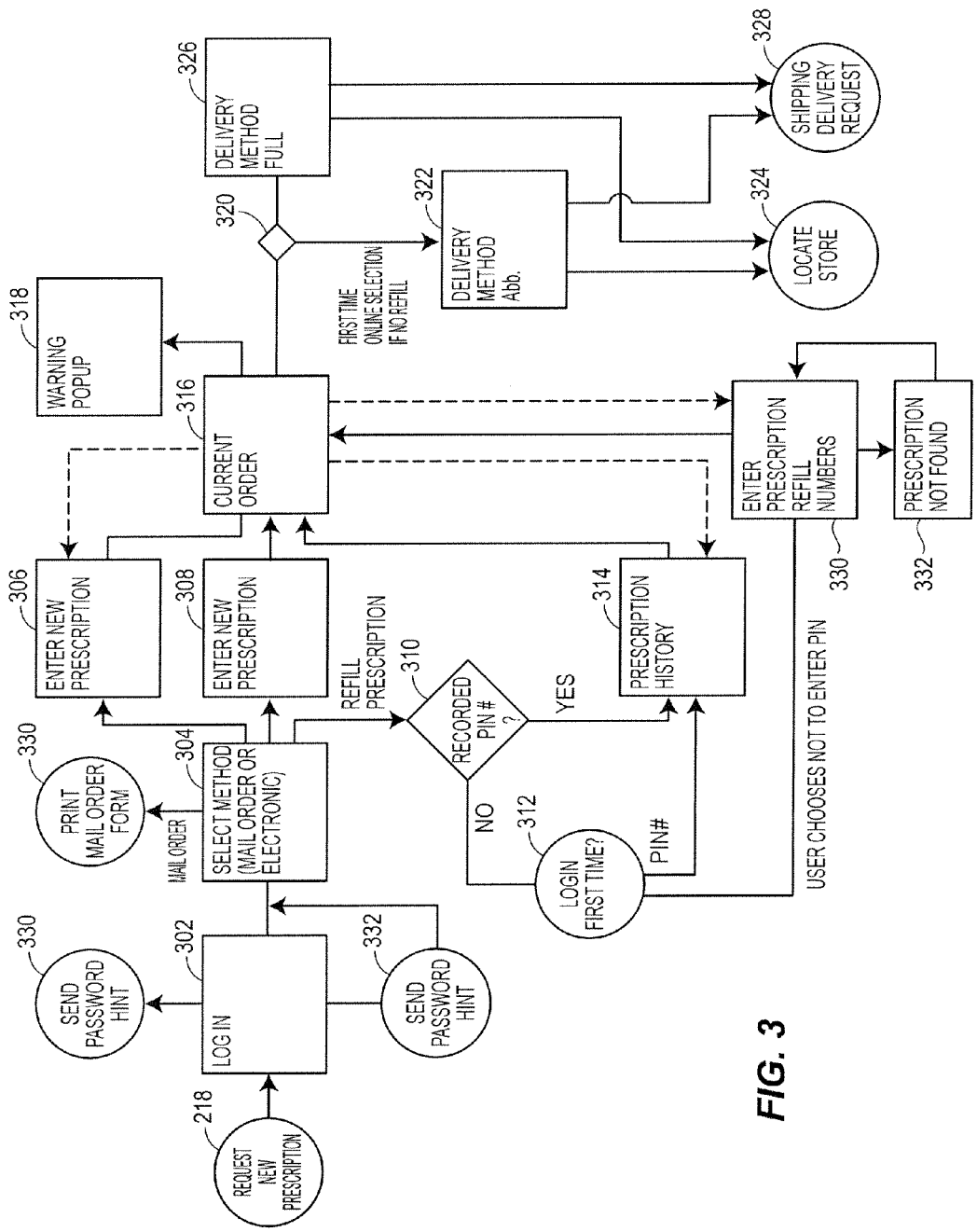
FIG. 3 illustrates a process for requesting new prescriptions via the internet website according to the teachings of the present invention.

FIG. 3 illustrates the process for requesting new prescriptions as indicated by link 218 in FIG. 2. After a user has navigated to the order or request new prescription area 218 from either the home page or the pharmacy home page, the user logs in the website using a user name and password as shown in block 302. If the user has not previously registered, flow proceeds to block 332 where the individual may proceed with a short registration as will be illustrated in FIG. 6. Once the individual is registered flow proceeds to block 304 where the user may select a method or source of the prescription. If the user has entered an incorrect user name and password at the login 302, a user may request a password hint to be sent via e-mail as indicated by block 330.

At block 304, the user has the option to print a mail order form 334, which can be used by the customer to manually fill-out and mail to a pharmacy store. At this point the process ends if the customer selects this particular option. In the alternative, if the user desires the prescription to be mail ordered or electronically transmitted to a particular pharmacy location for pick up flow proceeds from block 304 to three possible options.

The first option, shown in block 306, is transfer from another pharmacy company, for example. At step 306 the customer enters information about the prescription they are transferring (i.e., the drug name). Other information such as the previous pharmacy name, telephone number, prescription strength, prescription number, drug quantity, doctors name and the doctors phone are input by the user. Flow then proceeds to a "shopping cart" displaying the current order as illustrated at block 316. A dashed line from block 316 back to block 306 indicates that the customer may return from the "shopping cart" to either change the order or add additional prescriptions.

The second option available to the user is to enter a new prescription as illustrated at block 308. Here the customer is prompted to enter information about the new prescription to be filled including doctors name and phone, the drug name, strength and drug quantity. Flow then proceeds to the "shopping cart" displaying the current order at block 316.

The final option available to the user is to refill a prescription. Flow proceeds from block 304 to decision block 310 where the process quarries whether a recorded personal identification number has been entered by the user. That is, a user is given an option to simply enter a prescription number, which is particular to the users specific prescription to be refilled. If no recorded personal identification number has been entered, flow proceeds to block 312 where it is determined whether or not this is the users first time logging in. Here the user is given the option to log in using a personal identification number and, if the customer enters the personal identification number, flow proceeds to a prescription history display as shown in block 314. If the user chooses not to enter a personal identification number, the users then prompted to enter the prescription refill number at block 330. If the prescription number is invalid or not found the user is notified at block 332 that the prescription has not been found and prompted to reenter the prescription refill number. Once the prescription refill number has been entered flow proceeds to the "shopping cart" as indicated by block 316. Alternatively, if at either block 310 or block 312 the customer has entered a personal identification number, the flow proceeds to block 314 where a prescription history is displayed. From the screen a user may simply select refill of one or more particular prescriptions displayed. Flow then proceeds to the "shopping cart" displaying the current order in block 316.

After all the prescriptions are added by the customer into the "shopping cart" and has chosen to complete their order flow then proceeds to decision block 320. Additionally, the user is given the option to cancel their order where upon a warning pop-up 318 is shown so that the customer can definitively chose to cancel the order or continue with the order.

At decision block 320 it is determined whether this order is the customers first order and if the customer is refilling a prescription they have received at a particular pharmacy store location. If the user is selecting on-line for the first time the user is given a choice as to the delivery method in block 322. Here the user may select between either having the order shipped from one or more distribution facilities, such as one or more shipping facilities, or may locate and select a pharmacy store for pick-up of the prescription. If the user selects shipping delivery as indicated at block 328 the order is sent to a shipping facility where the prescription is filled and mailed out. Otherwise, an order for the prescription is sent to the store location selected at block 324 which automatically receives the prescription order via the application server 108 and interne server 112 as shown in FIG. 1. The order is then processed and filled by personnel at the pharmacy store location selected. If the order is not the users first order as determined at decision block 320, the user is given the option to select the last pharmacy store location they used and information such as the store number. address, pharmacy phone and pharmacy hours may be displayed. Otherwise, the user may also select a shipping delivery request for mailing of the prescription or locate and select another store for pick-up.

Figure 4:
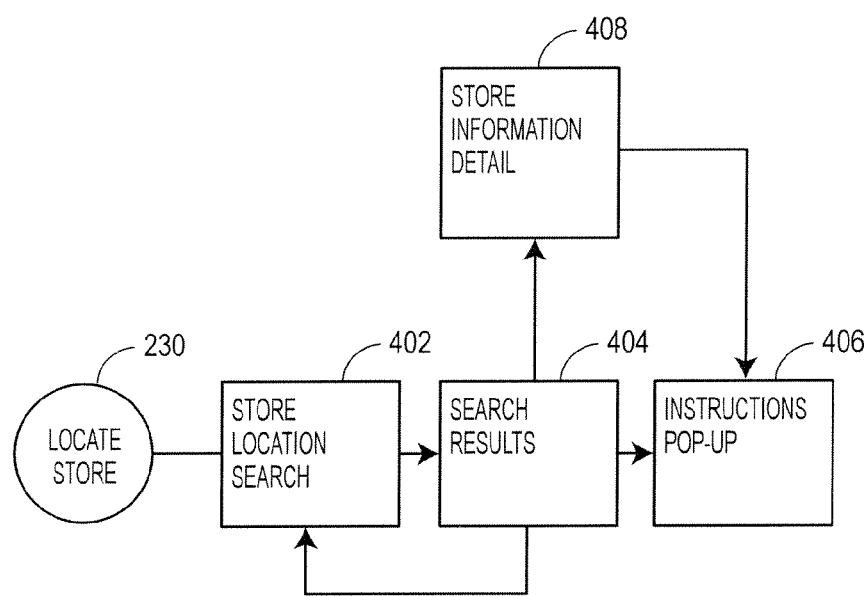
FIG. 4 illustrates a process for locating a particular pharmacy store via an internet website according to the teachings of the present invention.

FIG. 4 illustrates in further detail the process that is executed to locate a pharmacy store location as indicated by block 230 in FIG. 2. Once a user request to locate a store is received, a store location search is performed at block 402 after the user inputs information such as address, city, state, zip code, whether or not the store location is open 24 hours, has a drive through or within a search radius selected from various amounts of distance. Once the search is complete the results are displayed as shown at block 404 where the customer can select a store to view more details concerning the store as indicated by block 408 or may search again as indicated by the return arrow to block 402. Additionally, driving instructions may be shown in a pop-up as indicated by 406 either directly from the search results or after viewing the particular store information details.

Figure 5:
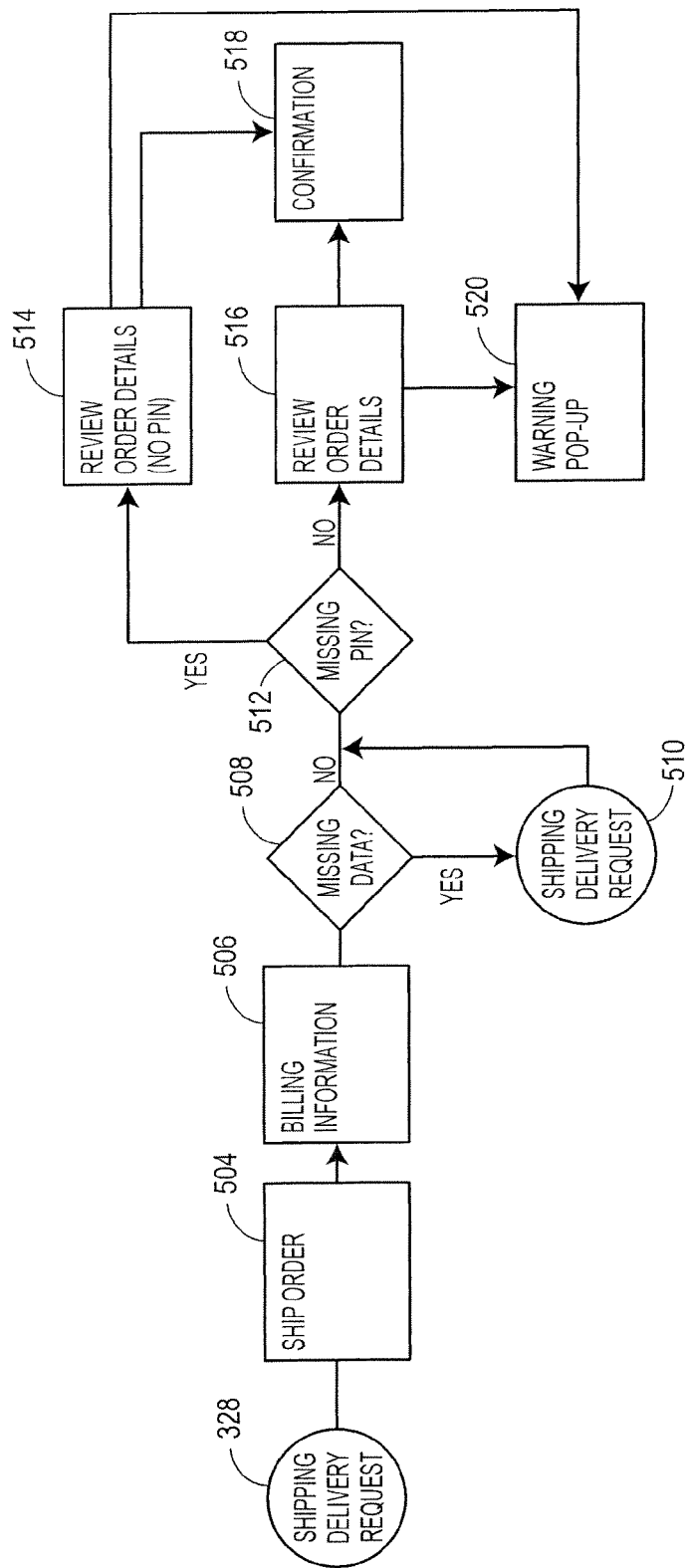
FIG. 5 illustrates a process for requesting shipping delivery of prescriptions via an internet website according to the teachings of the present invention.

FIG. 5 illustrates in further detail the processing of a shipping delivery request 328 as shown in FIG. 3. After a shipping delivery request is registered a command to ship the order 504 is executed. Here the customer is allowed to select or enter an address to have their order shipped to and the shipping method (e.g., U.S. Mail, FedEx, etc.). The customer then submits this information and next billing information is requested as shown at block 506. In block 506 the customer is either prompted to enter billing information, such as credit card information and address information. Additionally, the customer can elect to have new payment information saved to their profile or, if the information has already been saved may simply select to be billed according to the previously entered billing information. The flow then proceeds to decision block 508 which determines if there is any missing information. If there is missing information, flow proceeds to block 510 where the user is prompted to enter further registration information required for complete registration of an individual user. Once this is accomplished flow proceeds to decision block 512. If no missing data is determined at decision block 508 flow proceeds also to decision block 512 where it is determined whether or not the user has entered a personal identification number. If not the customer is prompted to review the order details in block 516. If no personal identification number was entered then the user is prompted to review the order details without information concerning refills other than the type and prescription number. From both blocks 514 and 516 flow proceeds to a confirmation screen confirming that the order has been placed as shown at block 518 and a corresponding e-mail is subsequently sent to the customer confirming receipt of the order. In addition, a warning pop-up 520 is shown to the user reminding the customer that the pharmacy company will be contacting the prescribing doctor if required by the particular law of the jurisdiction in which the user resides. In addition, the customer is informed that an e-mail will be sent when the prescription is ready.

Figure 6:
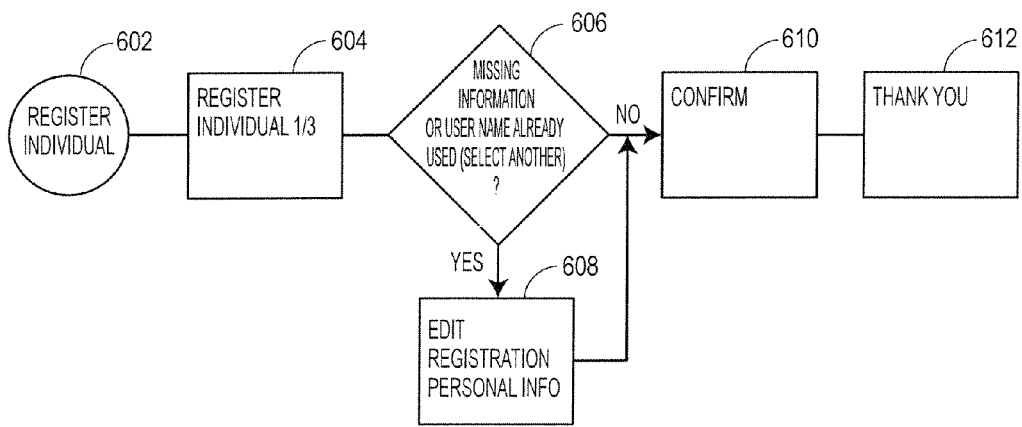
FIG. 6 illustrates an abbreviated method for registering an individual user with an on-line pharmacy website according to the teachings of the present invention.

FIG. 6 illustrates the process for registering individuals in an abbreviated manner such as is accomplished in step 332 of FIG. 3, for example. This abbreviated registration of individual users is intended to allow the users who are new to the on-line pharmacy website the ability to register for extended services without going through the full registration process. Once it is determined in step 602 that the individual user desires to register with the on-line pharmacy website flow proceeds to step 604 wherein the customer is prompted to provide personal data for registration. Such information includes name, a user name, a password, a password hint, gender, date of birth, e-mail address, home address, home phone, work phone and an indication in whether they wish to receive e-mails from the pharmacy company. The information is then submitted by the user wherein the website determines at decision block 606 whether information is missing or the user name selected by the individual user has already been used. If there is any information missing the flow proceeds to 608 wherein the user is allowed to edit the registration information entered by the user. Once this is accomplished flow proceeds to a confirmation screen 610 where the information may be checked by the user for potential errors and the customer then is allowed to confirm the information if correct. Finally, a thank you page 612 is displayed to indicate to the user that registration has occurred successfully.

Figure 7:
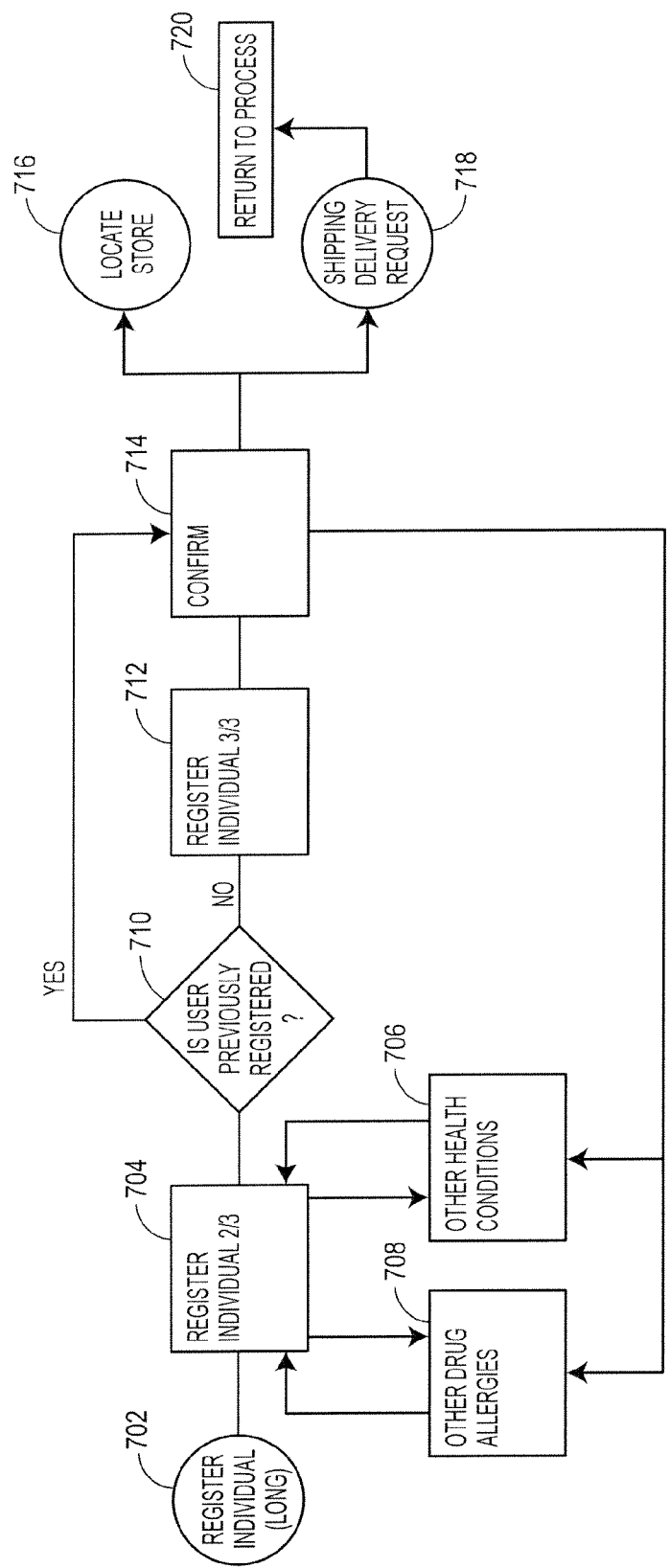
FIG. 7 illustrates a comprehensive process for registering an individual user in an on-line pharmacy according to the teachings of the present invention.

For those users who wish to utilize more of the functions offered on the website; a normal individual registration process is followed as illustrated in FIG. 7. Here the individual is prompted to input information at block 704 including the particular users health history, health conditions and allergies. To assist the user in entering health conditions in allergies screen 706 and 708 are available that list conditions and allergies from which the user may select. Additionally, the individual user is also requested to enter the same type of information as was entered in the abbreviated registration process illustrated in FIG. 6. The input of health conditions and drug allergies allows other features such as checking drug interactions and also alerting a user as to potential side effects that may result from existing health or allergy conditions and potentially prevent the occurrence of such side effects. After the information has been entered in block 704 the flow proceeds to decision block 710 where it is determined whether or not the user has previously registered using the abbreviated registration. If the user has flow simply proceeds to a confirmation screen 714. If not the individual is then prompted to input the remaining registration information that was required in the abbreviated registration process as illustrated in FIG. 6. Once this information is complete and accurate the user is directed to the confirmation screen 714. Additionally, the user may access the drug allergies and health conditions pages 706 and 708 from the confirmation screen if any other health conditions or allergies need to be added or deleted. Once the user has confirmed the registration information at 714 the user may either locate a pharmacy store location that they wish to pick-up prescriptions from or initiate a shipping delivery request if they are in the process of ordering a prescription. The flow then proceeds to block 720 which returns to whatever process the individual user is undergoing at the present time.

Figure 8:
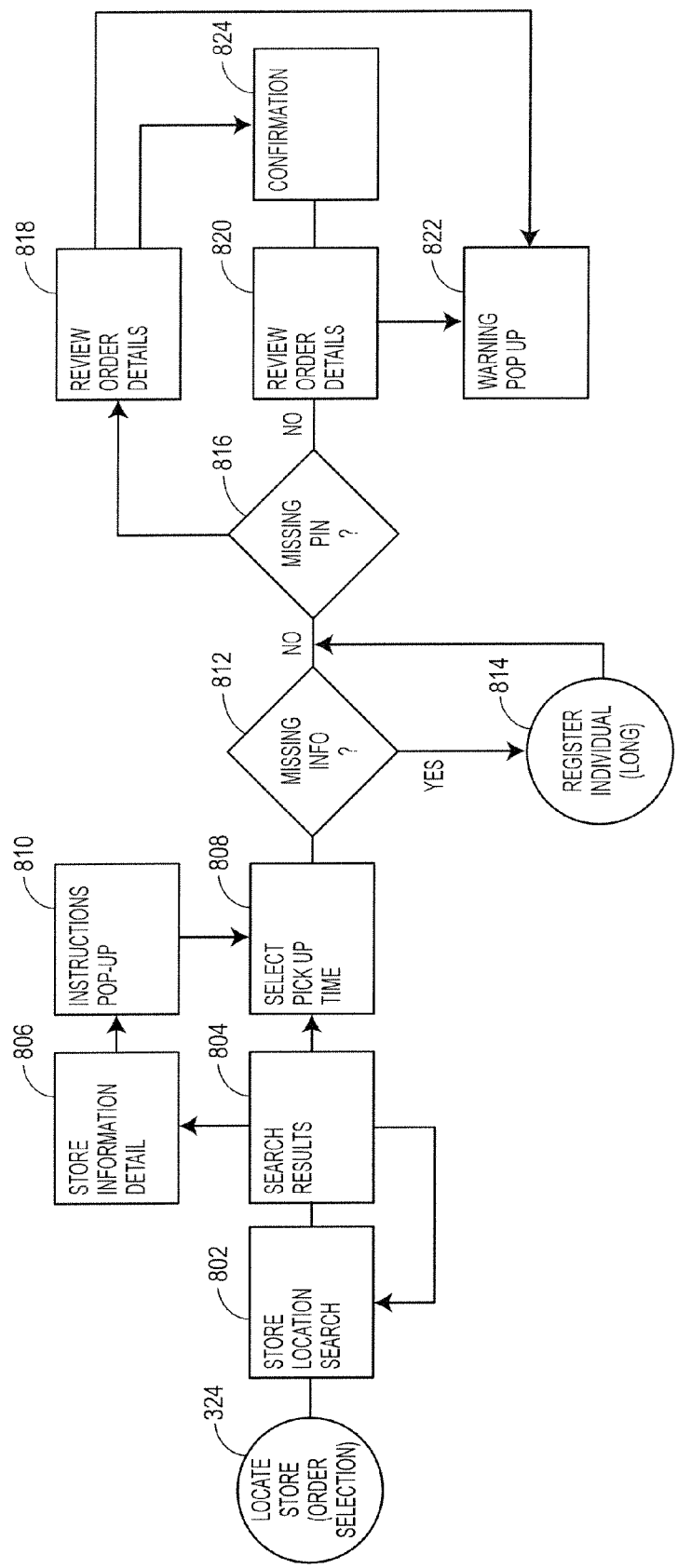
FIG. 8 illustrates a process of locating a store as part of a procedure for selecting a prescription order at an on-line pharmacy website according to the teachings of the present invention.

FIG. 8 illustrates the store location selection process used by an individual user when undergoing a prescription order selection. Here flow proceeds from step 324 as shown in FIG. 3, for example, here the user is allowed to locate a particular pharmacy store by first searching at step 802. The user is prompted to input search criteria similar to those previously described with respect to step 402 in FIG. 4. Once the search results are delivered at page 804 the user may either view store information detail and instructions to the store as shown in pages 806 and 810 before selecting a pick-up time at page 808 or simply proceed from the search results 804 to selecting a pick-up time 808. In a preferred embodiment, the pick-up time has a default time that is predetermined and must be actively changed by the individual user if a different time is desired. Next flow proceeds to decision block 812 where it is determined whether or not there is missing information. If so, flow proceeds to register the individual at page 814, which corresponds to the registration start block 702 as illustrated in FIG. 7. If no information is missing or once registration has been completed flow then proceeds to decision block 816 to determine whether or not there is a missing personal identification number. If the personal identification number is not missing the user is shown a screen 820 to review the order details and subsequently confirm the order detail in screen 824. In addition, a warning pop-up 822 appears to alert the customer that the users doctor will be contacted, if required. A subsequent e-mail is then sent to the user confirming the order and also a follow-up e-mail may be sent when the order has been filled. In the alternative, if the personal identification number is missing the user is shown a screen to review the order details 818 without refill information and subsequently the order is confirmed as shown by page 824 and the appropriate warning 822 is also shown to the user.

Figure 9:
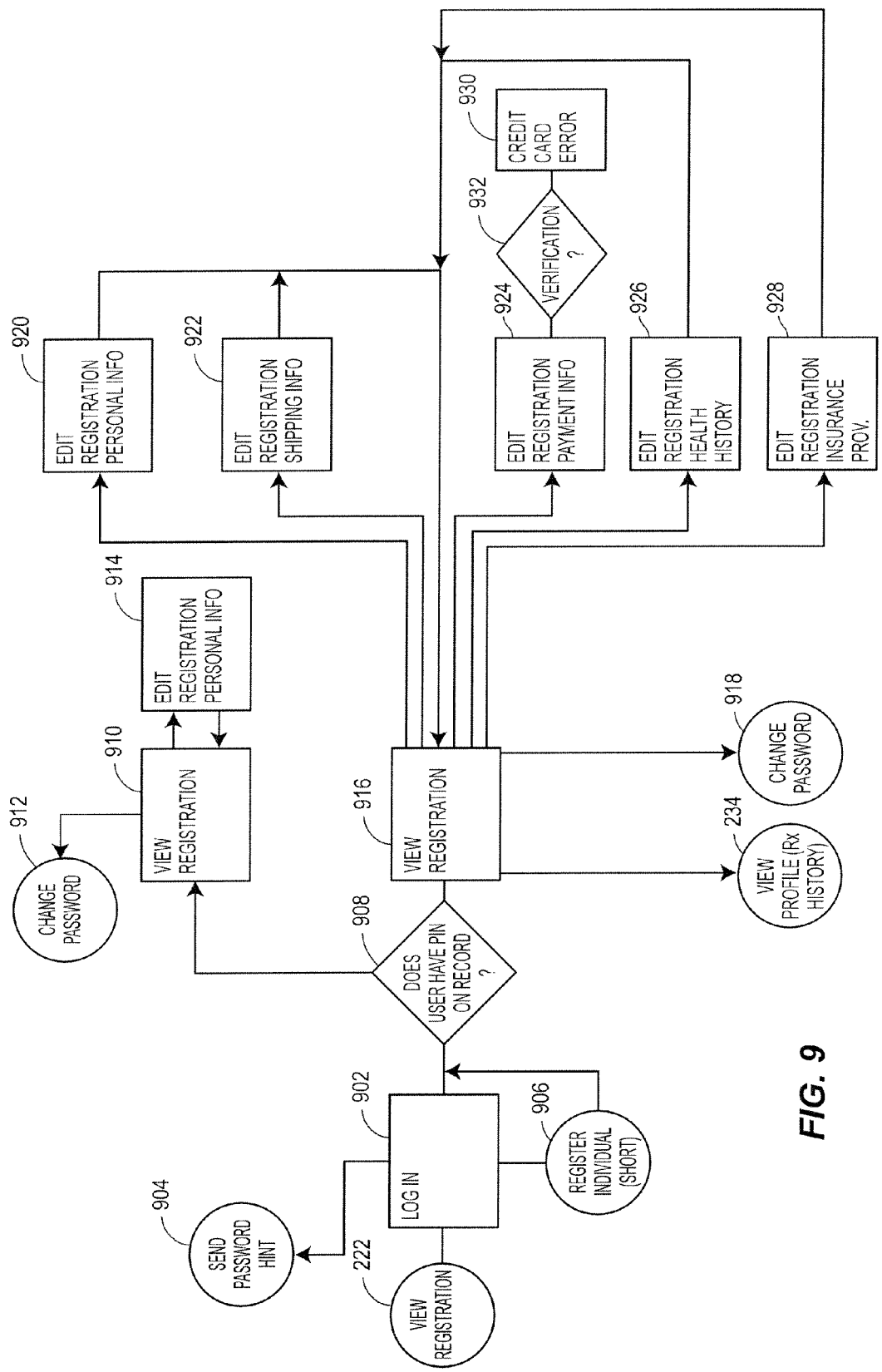
FIG. 9 illustrates a process for allowing a user to view registration information with an on-line pharmacy website according to the teachings of the present invention.

FIG. 9 illustrates the process by which a user may view and edit their registration information from the pharmacy home page 204, as shown in FIG. 2. When a user selects to view their registration at screen 222, a login screen 902 is presented to the user. The user enters a username and password, which is verified by the network server 106. If the user has forgotten their password, a request for sending a password hint may be performed as indicated by screen 904. If the user has not yet registered, the user may also proceed to the abbreviated registration at screen 906 and complete the process illustrated in FIG. 6. After the user has successfully logged in, the flow proceeds to decision block 908, where a determination is made whether the user has a personal identification number (PIN) on record.

If a user does not have a PIN on record, a view registration screen 910 is displayed to allow the user to view their particular registration information and edit personal registration information (914) or change their password (912). Alternatively, if the user has a PIN on record, a screen 916 for viewing their registration history is shown with links to screens for editing personal registration information (920), as well as registered shipping information, payment information (924), health history (926) and insurance provider information (928). Additionally, the user has the option to change their password as shown at step 918 or view their profile (prescription history) with a link screen 234 to the start of the history viewing procedure, which will be described later in regard to FIG. 10. Also, the view registration procedure illustrated in FIG. 10 includes a verification step 932 in which credit card payment information, for example, is verified or authenticated. If the credit card information is not verified at step 932, a credit card error screen 930 indicates to the user that there was an error in verification.

Figure 10:
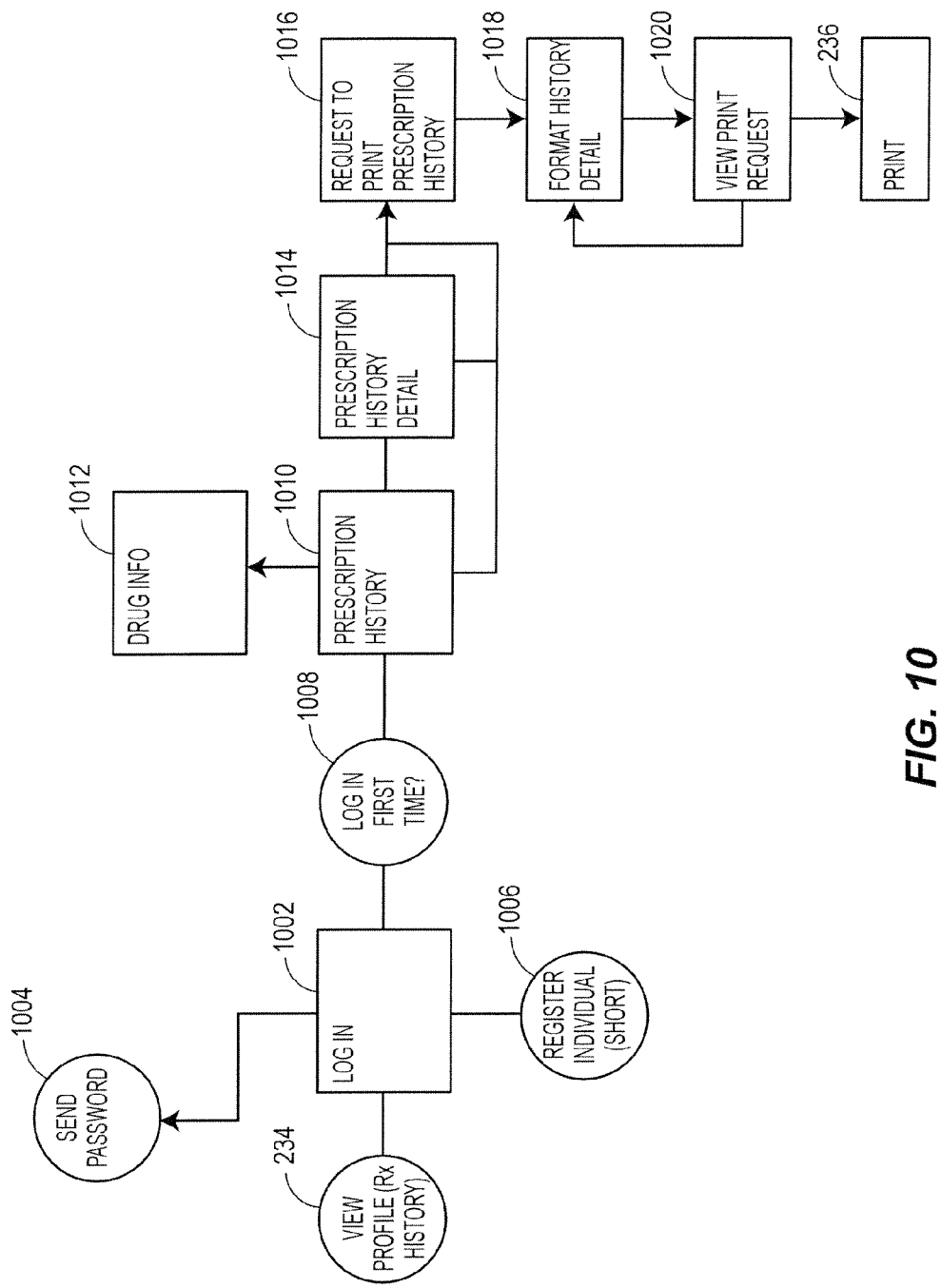
FIG. 10 illustrates a process for viewing a user's prescription history and profile as well as formatting and printing the history according to the teachings of the present invention.

FIG. 10 illustrates a procedure according to the teachings of a preferred embodiment that allow users to view their profile/prescription history. After the user requests to view their profile/prescription history, the user is prompted to log in at screen 1002 by entering a username and password. The user enters a username and password, which is verified by the network server 106. If the user has forgotten their password, a request for sending a password hint may be performed as indicated by screen 1004. If the user has not yet registered, the user may also proceed to the abbreviated registration at screen 1006 and complete the process illustrated in FIG. 6.

Next, the process proceeds to a determination of whether or not this is the user's first login to the profile/prescription history viewer. If it is the first time that the user has logged in, a personal identification number (PIN) must be assigned to the user before accessing further information according to a preferred embodiment. This is to ensure a further degree of security for personal information of the user. However, it is noted that such degree of security is not necessarily required, merely desirable. The step 1008 prompts the user for a PIN. If the user does not have a PIN, a process is invoked to assign a PIN to the user. This process will be described later in connection with FIG. 15. Once the user has entered a correct PIN number the customer is shown their prescription history that is stored in the customer database 110. Such information can included, but is not limited to, prescription number, refills remaining, drug name, drug strength, the doctor's name, last fill date and refills remaining.

From the prescription history screen 1010, various further information can be displayed. For example, drug information can be hyper-linked from the prescription history screen 1010 to allow display of specific drug information at screen 1012, including, for example, images of the particular medications and pricing information. Also from the prescription history screen 1010, further details concerning each piece of information given in the prescription history screen 1010 may hyper-linked to a prescription history detail screen 1014.

The process for viewing a user's profile/prescription history also features steps enabling the user to format and print their prescription history. From either the prescription history 1010 or the prescription history detail 1014, a user may request to print their prescription history at step 1016. The user is then allowed to select the formatting of the prescription history to be printed at screen 1018. For example, the user may select which type of information they wish to be displayed and in what order the information is be listed. Various other formatting options that may be available to user is desired. Once the user has selected the desired printing format, the print request is made viewable in screen 1020 and the user either has the option to accept the format and print at step 236 (corresponding to step 236 illustrated in FIG. 1) or return to the formatting screen 1018 for further editing of the format.

Figure 11:
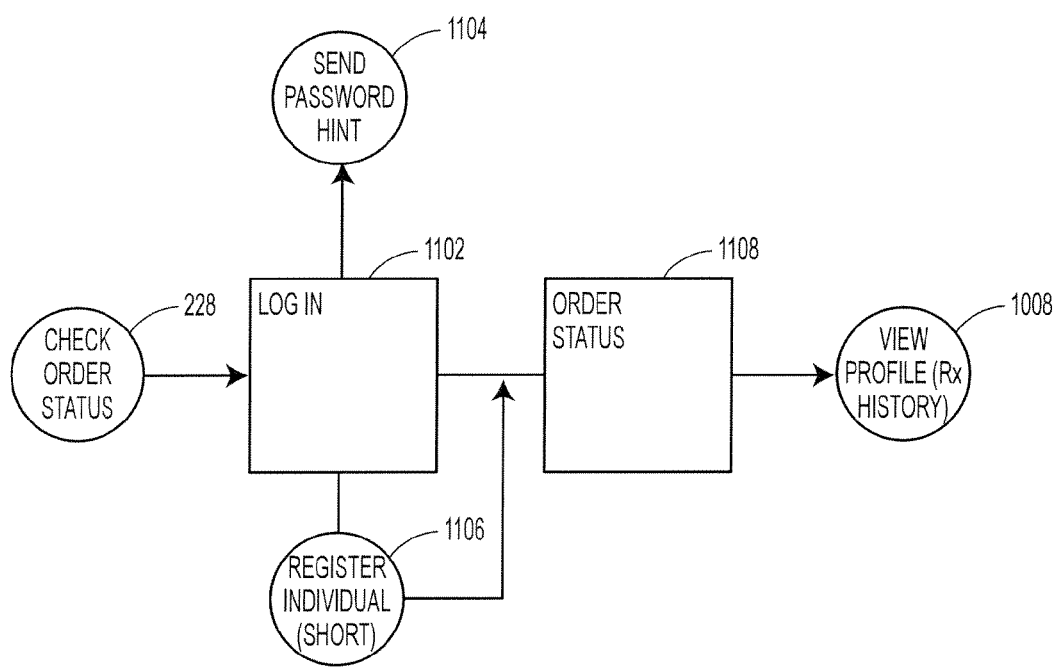
FIG. 11 illustrates a process by which a user of an on-line pharmacy website may check status of a prescription order according to the teachings of the present invention.

FIG. 11 illustrates a process for checking the status of a prescription order that has been placed. When a user selects the check order status screen 228 from the pharmacy homepage 204, the user is then prompted to login at step 1102 by entering a username and password. The user enters a username and password, which is verified by the network server 106. If the user has forgotten their password, a request for sending a password hint may be performed as indicated by screen 1104. If the user has not yet registered, the user may also proceed to the abbreviated registration at screen 1106 and complete the process illustrated in FIG. 6. Once the user has logged in, a screen 1108 displaying the status of currently pending orders including information such as the date received, the order number, total amount charged and order status (e.g., shipped, in-process, etc.). The user is also allowed to view their prescription history by linking to screen 1008 shown in FIG. 10.

Figure 12:
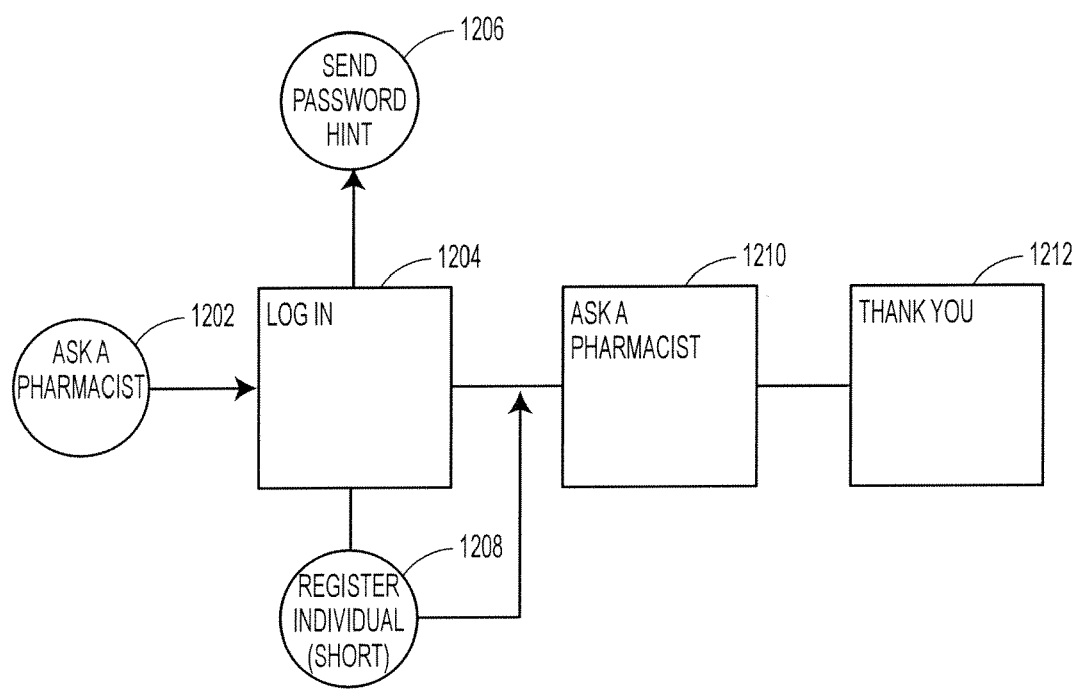
FIG. 12 illustrates a process to submit questions to a pharmacist via an on-line website according to the teachings of the present invention.

FIG. 12 illustrates a feature of the pharmacy website that enables users to submit questions they may have to a pharmacist. This feature may be accessed from the pharmacy home page 204 or may also be accessed from other pages, such as the prescription ordering screens, if desired. When a user selects the "Ask a Pharmacist" feature at 1202, the user is then prompted to login at step 1204 by entering a username and password. The user enters a username and password, which is verified by the network server 106. If the user has forgotten their password, a request for sending a password hint may be performed as indicated by screen 1104. If the user has not yet registered, the user may also proceed to the abbreviated registration at screen 1106 and complete the process illustrated in FIG. 6. Once the user a logged in, a screen 1210 is displayed enabling the user to input and submit a question that will be delivered either directly via the network server 106 or via the intranet server 112 to a pharmacist. After the question has been submitted, a thank you screen 1212 appears to inform the user that the question has been successfully transmitted.

Figure 13:
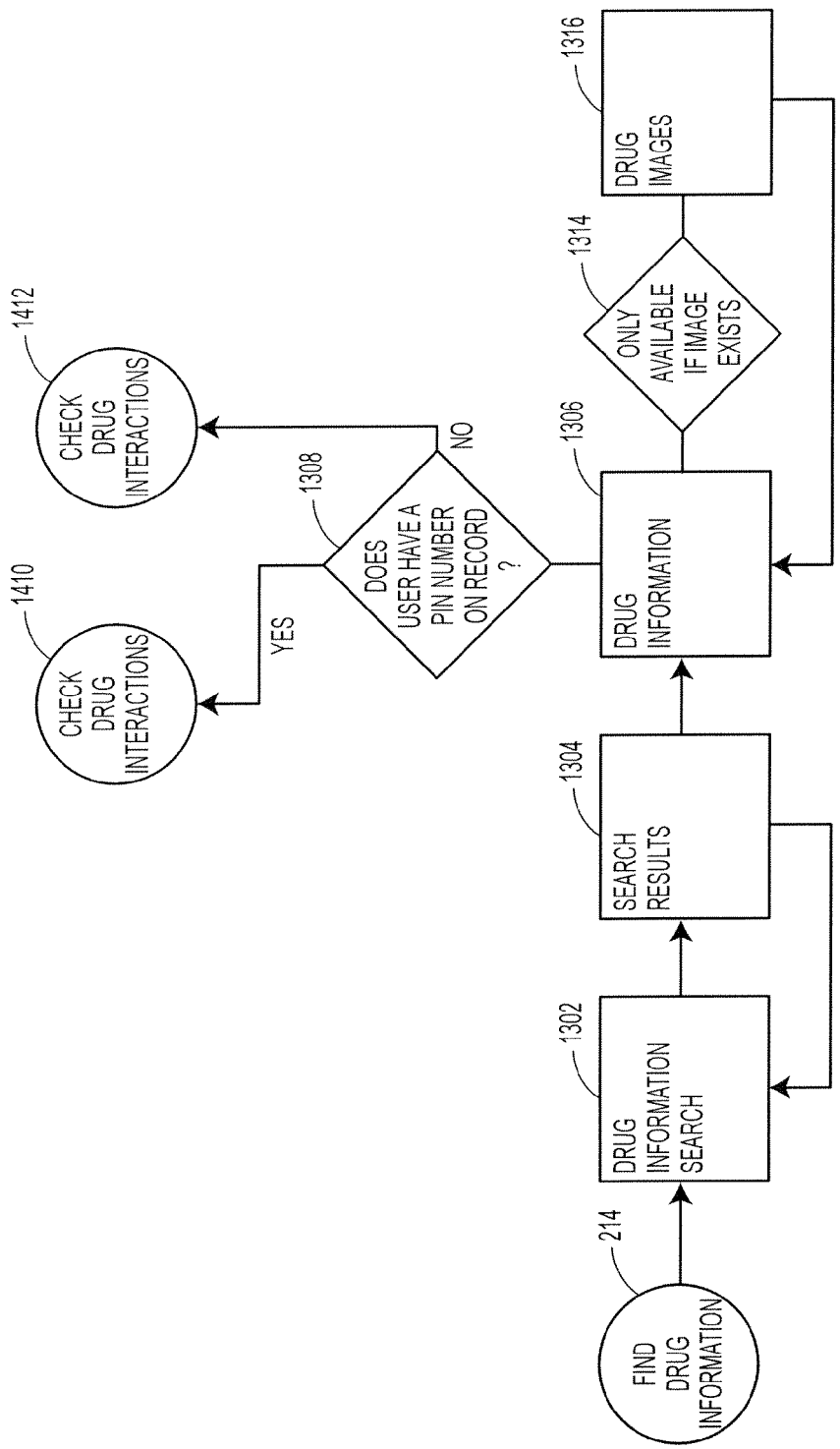
FIG. 13 illustrates a process for finding drug information using an on-line website according to the teachings of the present invention.

Another feature of the pharmacy website is access to a repository of drug information. FIG. 13 illustrates a process that enables a user to access various drug information. In step 214, the user requests to find specific drug information. Screen 1302 is displayed enabling the user to enter or select search criteria. For example, the user may select a letter of the alphabet, which causes an alphabetical list of drugs beginning with that letter to be displayed and from which the user may select a particular drug. Another example would be allowing the user to enter the name or partial name of a drug, and a list of pharmaceuticals that match the user entry is displayed. The repository of drug information is searched and the search results are displayed to the user in screen 1304. If the search does not yield results or yields irrelevant results, the user may return to the search entry screen 1302 to refine or change the search query.

From the search results displayed in screen 1304, the user may select which results they wish to view. After selecting one or more results, the information concerning the particular drugs is displayed in screen 1306. The information may includes pricing, dosage, commonly prescribed quantity, price of the most commonly prescribed quantity, the generic name, common uses and precautions. Also if an image of the drug exists in the information repository as determined at block 1314, the drug images may be displayed to the user at screen 1316.

An additional feature allows the user to check drug interactions with the particular drug selected. Prior to procession to the drug interaction check, a determination is first made whether the user has an assigned personal identification number (PIN). If the user has a PIN, the flow proceeds to screen 1410, which will be described in connection with FIG. 14. For users not yet having an assigned PIN, the flow proceeds to screen 1412, which will also be described in connection with FIG. 14.

Figure 14:
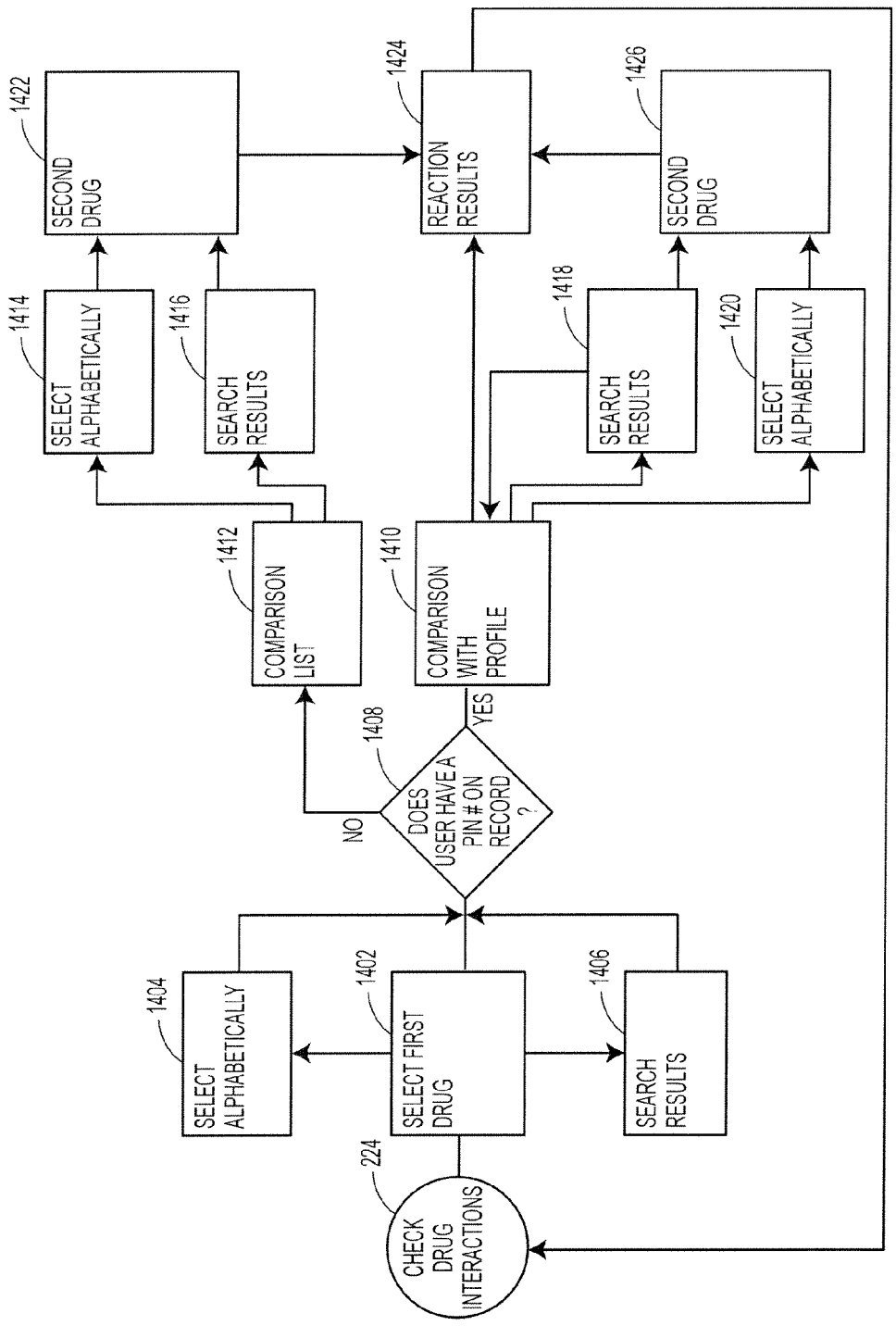
FIG. 14 illustrates a process for checking drug interactions via an on-line pharmacy website according to the teachings of the present invention.

In FIG. 14, the user is allowed to check drug interactions from either the pharmacy home page 204 or the health library home page 210, both shown in FIG. 2. Also, as described above, the drug interaction check process may also be entered from the find drug information process illustrated in FIG. 13. When a user selects the checking of drug interactions at screen 224, the user is prompted to select a first drug at screen 1402 from either an alphabetical listing of drugs in step 1404 or by direct input or search as illustrated by screen 1406.

Next, a determination, is made whether the user has a PIN assignment. If the user does not, then a comparison list of drugs is displayed at screen 1412 from which the user may select. Similar to the selection of the first drug in step 1402, the user may select from an alphabetical list of drugs in screen 1414 or search for a particular drug 1416 and then select a second drug from either screen, the choice displayed at screen 1422. Once the second drug is selected, the reaction results are displayed to the user at screen 1424.

If the user has a PIN assignment as determined at step 1408, a comparison with the user's profile the drugs presently in the user's profile or personal prescription history stored in the database 110 is performed and the results of the comparison are displayed in a reaction results screen 1424. Also, at screen 1410, if the user wishes to compare with another drug not in the user's profile or personal prescription history, the user has the option to search for particular drugs or select from an alphabetic list of drugs, the user may so choose as indicated by screens 1418, 1420 and 1426. The user may then select the second drug and compare with the first drug, the results being displayed in the reaction results screen 1424.

Figure 15:
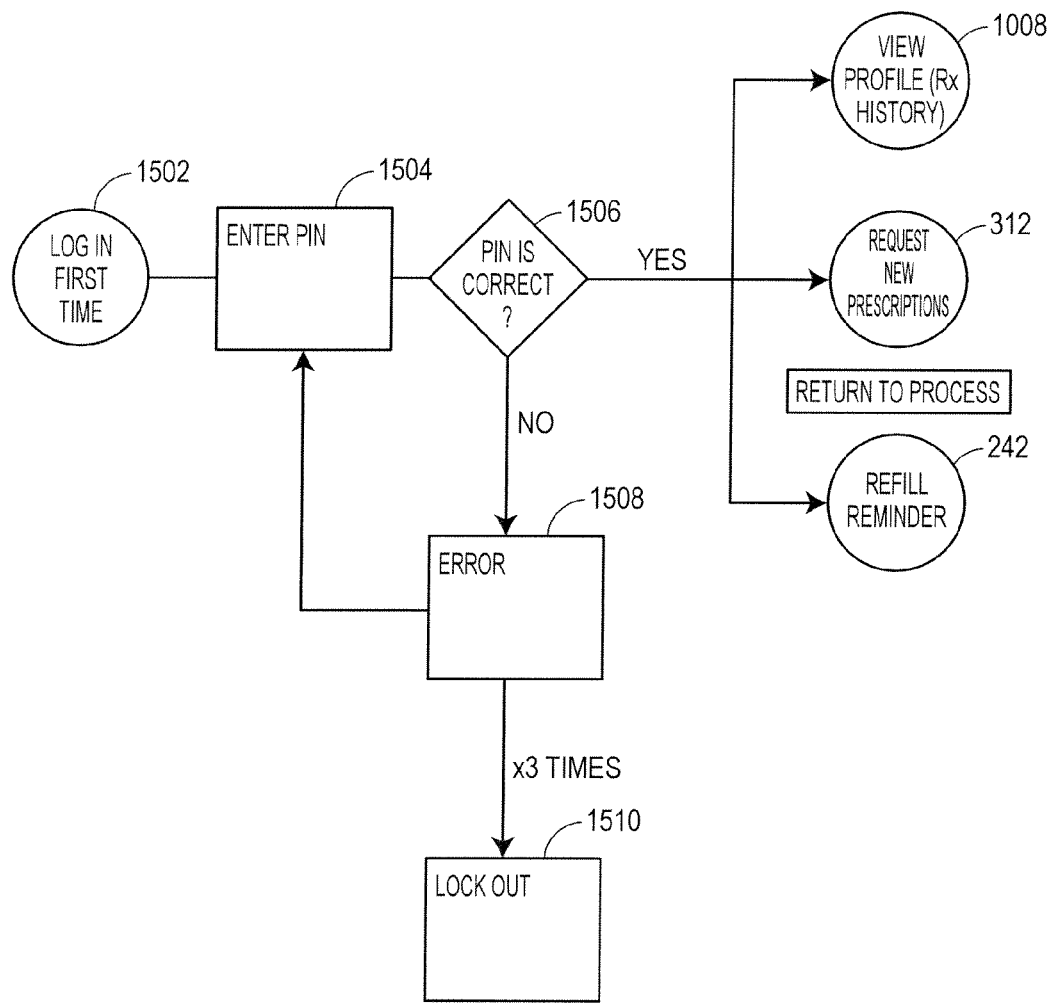
FIG. 15 illustrates a process undertaken for viewing a user's prescription history during a first time login to an on-line pharmacy website according to the teachings of the present invention.

FIG. 15 illustrates the process by which a user may associate a PIN when logging in for the first time to particular portions of the pharmacy website. Preferably, the PIN is delivered after initial registration to the user either by U.S. mail or any other means of communication by which the PIN may be securely communicated to the user. Once the user has received the PIN, the routine of FIG. 15 may be initiated, a screen 1504 is displayed prompting the user to enter the PIN. The server 106 then checks whether the PIN entered is correct at block 1506. If the PIN is not correct, a error screen 1508 is displayed indicating that the PIN is incorrect. The user may re-enter the PIN by returning to screen 1504. However, if an incorrect PIN is entered three times, the server locks out re-entry of the PIN for that particular user as indicated by screen 1510.

Alternatively, when a correct PIN is entered the association is performed and the process returns to whatever previous process was being performed when the first time login process was invoked. As shown in FIG. 15, these may include viewing profile/prescription history (screen 1008), requesting a new prescription (screen 312) or during the request for a refill reminder (screen 242 as shown in FIG. 2).

Another feature of the system shown in FIG. 1 is the ability to register users with the on-line pharmacy website via the intranet server 112. An exemplary methodology includes soliciting contact information (e.g., an e-mail address or a postal address) and other pertinent information from a potential user when they visit a member pharmacy store location. Personnel at the member pharmacy store then enter the information concerning the user into a connection to the intranet server 112 located at the member pharmacy store, which is then associated with information concerning the user previously stored in the database 110 via the connection through the application server 108 and also with the network server 106. The user is then sent a user name and a password based on the contact information via an e-mail or U.S. mail, for example, with which the user may log on to the on-line pharmacy website. This methodology enables a user to conveniently register while visiting a member pharmacy location without having to first access the website via the Internet. Hence, the registration process is essentially "click-free" to the user. The location of the connections to the intranet server could also be located in other centralized locations of the particular pharmacy company or network of pharmacy companies, such as a pharmacy company headquarters or other office and warehouse locations of the particular pharmacy company Using the above methodology, when the pharmacy personnel register the user, a search for the customer/user is first performed on a utility residing on the intranet server 112. The search terms may include the user's prescription number, name, phone number, birth date to locate the user. Of course, certain terms such a the prescription number will return an exact match, whereas terms such as the user's name or birth date may yield multiple matches from which the pharmacy personnel will have to determine the correct match for the particular user. Other methods of locating a user may include accessing the user's specific information from the customer database 110 and allowing execution of registration from this particular accessed information.

Once the correct user is located and selected, the personnel enter the user's e-mail address, for example, and any other pertinent information that may not be previously recorded (e.g., phone number, date of birth, postal address, etc.). After all desired information has been entered, a registration command is sent to the application server 108, which sends the command to the network server 106, which performs registration for the user, and to the customer database 110 for association of the user's registration with the user's information stored therein. After registration is complete, an e-mail, for example, is sent to the user by the network server 106 that includes the username and password, which the user may use to log in to the on-line pharmacy website.

Although certain methods and apparatus constructed in accordance with the teachings of the invention have been described herein, the scope of coverage of this patent is not limited thereto. For example, the particular organization of the on-line pharmacy website shown in FIG. 2 is not limited to only this one possible arrangement, but is merely one of many possible organizations that could be employed to implement an on-line pharmacy website in accordance with the teachings of the present invention. On the contrary, this patent covers all embodiments of the teachings of the invention fairly falling within the scope of the appended claims either literally or under the doctrine of equivalents.

What is claimed is:

1. A system for accessing pharmacy data and ordering prescriptions via a network comprising:
    a network server connected to the network that is accessible by one or more customers via the network;
    a database containing information concerning drugs and personal information concerning one or more of the customers, wherein the personal information includes a prescription drug history of each respective one of the one or more customers; and
    an intranet server that is connected to at least a plurality of member pharmacies and one or more shipping facilities;
    an application server connected to the network server, the database and the intranet server to integrate the network server, the database, and the intranet server,
    wherein the application server is configured to:
        receive a username and password from a customer;
        cause a browser to display to the customer the information concerning drugs and personal information concerning that customer if the username and password are confirmed, and
        cause the browser to display an option to transmit a prescription order to: at least one of the plurality of member pharmacies or one of the one or more shipping facilities,
        receive the prescription order and perform a prescription drug interaction check;
        receive an indication of a choice from the customer relative to the option;
        when the customer chooses the option to transmit the prescription order to the one or more shipping facilities, execute a command to the one of the one or more shipping facilities via the intranet server, so that at least one prescription drug associated with the prescription order is shipped from the one of the one or more shipping facilities; and
        when the customer chooses the option to transmit the prescription order to one of the plurality of member pharmacies for pick-up by the customer, transmit via the intranet server the prescription order to one of the plurality of member pharmacies to be processed so that at least one prescription drug associated with the prescription order is filled at the one of the plurality of member pharmacies.

2. The system as defined in claim 1, wherein the network server is configured to format display of the prescription history of each respective one of the one or more customers according to a plurality of selectable display formats that are selected by the respective one of the one or more customers.

3. The system as defined in claim 2, wherein the network server is configured to allow each respective one of the one or more customers to print each particular selectable display format of the prescription history that is selected by the respective one of the one or more customers.

4. The system as defined in claim 1, wherein the prescription order includes at least one of ordering a new prescription, refilling an existing prescription and transferring a previous prescription from another entity previously filling the previous prescription.

5. The system as defined in claim 1, further comprising a link to a quiz concerning health issues.

6. The system as defined in claim 1, wherein the application server is further configured to display to the customer a name of a doctor that prescribed the at least one prescription drug, and display to the customer a generic alternative for the at least one prescription drug.

7. The system as defined in claim 1, wherein the application server is further configured to display to the customer the number of refills left for the prescription order.

8. The system as defined in claim 1, wherein the application server is further configured to send the customer a refill reminder email to remind the customer to refill the prescription.

9. The system as defined in claim 1, further comprising a hyperlinked image of a drug associated with the prescription order.

10. The system as defined in claim 1, wherein the application server is further configured to display a status of the prescription order.

11. A method enabling one or more customers to order prescriptions and access pharmacy data via a network comprising:
    accessing a network server hosting a network website via the network;
    registering a customer with the network website including prompting the customer to enter a username and password;
    displaying to the customer on the website a prescription order selection;
    displaying to the customer on the website a pharmacy data access selection;

when the customer selects the prescription order selection:
 displaying one or more prescription order displays to the customer on the website;
 receiving from the customer a particular prescription order;
 performing a prescription drug interaction check for the particular prescription order;
 sending the customer a confirmation email corresponding to the received particular prescription order,
 when the customer selects to pick up at least one prescription drug from one of the plurality of member pharmacies, transmitting, via an intranet server that is connected to at least a plurality of member pharmacies and one or more shipping facilities, the particular prescription order so that the at least one prescription drug associated with the particular prescription order is filled at the one of the plurality of member pharmacies;
 when the customer selects to have at least one prescription drug shipped from one of the one or more shipping facilities, transmitting, via the intranet server that is connected to at least the plurality of member pharmacies and the one or more shipping facilities, the particular prescription order so that the at least one prescription drug associated with the particular prescription order is shipped from the one of the one or more shipping facilities; and
 when the customer selects the pharmacy data access selection, displaying one or more pharmacy data access displays to the customer wherein the customer is allowed to access one of a personal prescription history and specific drug information from a database.

12. The method as defined in claim 9, wherein registering the customer further comprises:
 prompting the customer to enter personal profile information;
 transmitting an entered username, password and personal profile information to a network server;
 storing the username, password and personal profile information in the network server; and
 enabling the customer to access at least portions of the website by subsequent entry of the entered username and password.

13. The method as defined in claim 11, wherein the personal prescription history includes each of the current prescription, name of prescribing doctor, dosage, strength, drug name, a link to drug information, and the drug's price.

14. The method as defined in claim 11, wherein the method further comprises:
 assigning the customer a personal identification number subsequent to the step of registering the user;
 communicating the personal identification number to the customer via a secured communication; and
 prompting the customer to enter the personal identification number to allow the customer to access secured portions of the website.

15. The method as defined in claim 11, wherein the step of registering the customer further comprises:
 manually entering customer contact information and at least one of the username, the password and a customer personal profile concerning the customer into a connection to an intranet server located in one of any one of a plurality of member pharmacies and one or more centralized company locations;
 associating the customer to a network server; and
 communicating at least a username and password, which enable the customer to access the network website, to the user via a secured communication using the customer contact information.

16. The method as defined in claim 11, further comprising the steps of:
 enabling the customer to select one or more display formats for the personal prescription history; and
 enabling a customer to print a specific format selected by the customer from the one or more display formats.

17. The method as defined in claim 11, wherein the particular prescription order includes a selectable designation by the customer to communicate that the prescription will one of:
 a) be manually picked up at a selected pharmacy store location; or
 b) be shipped to a designated postal address.

18. A system for accessing pharmacy data and ordering prescriptions via a network comprising:
 a database containing information concerning prescription drugs and personal information concerning a portion of a plurality of customers; and
 an intranet server that is connected to a first member pharmacy, a second member pharmacy, and a shipping facility;
 an application server connected to the database and the intranet server to integrate the database and the intranet server,
 wherein the application server is configured to:
  receive a username and a password from a customer;
  allow the customer to access the information concerning prescription drugs and personal information concerning that customer if the username and the password are confirmed,
  provide each of the one or more customers with an option to: transmit a prescription order to the first member pharmacy or the shipping facility if the username and the password are confirmed;
  receive the prescription order and perform a prescription drug interaction check;
  receive an indication of a choice from the customer relative to the option to transmit the prescription order to the first member pharmacy or the shipping facility;
  send an email confirmation to the customer confirming the prescription order;
  cause a browser to display a status of the order;
  when the customer chooses the option to transmit the prescription order to the shipping facility, transmit, via the intranet server, the prescription order to the shipping facility so that at least one prescription drug associated with the prescription order is shipped from the shipping facility; and
  when the customer chooses the option to transmit the prescription order to the first member pharmacy, transmit, via the intranet server, the prescription order to the first member pharmacy so that at least one prescription drug associated with the prescription order is filled at the first member pharmacy.

19. A method enabling a customer to order prescriptions and access pharmacy data via a network comprising:
 providing a network server hosting a network website via the network;
 registering a customer with the network website that includes prompting the customer to input a username and password;
 displaying to the customer on the website a prescription order selection;

displaying to the customer on the website a pharmacy data access selection;
when the customer selects the prescription order selection and the username and password are confirmed:
  displaying a prescription order display to the customer on the website;
  receiving from the customer a particular prescription order for a prescription drug;
  performing a prescription drug interaction check;
  wherein the particular prescription order includes a selectable designation by the customer to communicate via the intranet server that the prescription will one of:
    a) be manually picked up at a selected pharmacy store location; or
    b) be shipped to a designated postal address;
  sending a confirmation email to the customer for the prescription order;
  receiving and storing medical insurance information for the customer;
  displaying to the customer pricing information for a drug in the prescription order;
  displaying to the customer a name of a doctor that prescribed the drug; and
displaying a pharmacy data access display to the customer when the customer selects the pharmacy data access selection and when the username and password are confirmed, and providing the customer access to one of a personal prescription history and specific drug information from a database.

20. A pharmacy system, comprising:
means for accessing a network server hosting a network website;
means for registering a customer with the network website;
means for displaying to the customer on the website a prescription order selection;
means for displaying to the customer on the website a pharmacy data access selection;
means for displaying one or more prescription order displays to the customer on the website when the customer selects the prescription order selection;
means for receiving from the customer a particular prescription order;
means for performing a prescription drug interaction check for the particular prescription order, and
means for sending the customer a confirmation email corresponding to the received particular prescription order;
means for displaying to the customer pricing information for a drug in the prescription order;
means for displaying to the customer a name of a doctor that prescribed the drug;
means for displaying to the customer a generic alternative for the prescribed drug;
means for transmitting the prescription order to a member pharmacy or a shipping facility, so that at least one prescription drug associated with the prescription order is filled at the member pharmacy or is shipped from the shipping facility; and
means for displaying one or more pharmacy data access displays to the customer when the customer selects the pharmacy data access selection wherein the customer is allowed to access one of a personal prescription history and specific drug information from a database.

* * * * *